United States Patent [19]

Murray, Jr. et al.

[11] Patent Number: 5,512,751
[45] Date of Patent: Apr. 30, 1996

[54] CALIBRATION OF NIR SPECTRA IN MEASURING PROPERTIES OF PETROLEUM PRODUCTS

[75] Inventors: Richard C. Murray, Jr., Palatine, Ill.; Mark S. Zetter, El Dorado Hills, Calif.

[73] Assignee: UOP, Des Plaines, Ill.

[21] Appl. No.: 358,288

[22] Filed: Dec. 19, 1994

[51] Int. Cl.$^6$ .................................................. G01N 21/35
[52] U.S. Cl. .................. 250/339.09; 250/339.12
[58] Field of Search .................. 250/339.09, 339.12, 250/343

[56] References Cited

U.S. PATENT DOCUMENTS 5,362,965  11/1994  Maggard ........................... 250/339.12

OTHER PUBLICATIONS

DiFoggio et al., "Near–Infrared Offers Benefits and Challenges in Gasoline Analysis", Oil & Gas Journal, May 1993, pp. 87–90.

*Primary Examiner*—Carolyn E. Fields
*Assistant Examiner*—Edward J. Glick
*Attorney, Agent, or Firm*—Thomas K. McBride; Eugene I. Snyder

[57] ABSTRACT

The observation was made that virtually all octane number variations arise from 23 components present in a broad variety of gasolines. Consequently it is possible to develop a calibration set consisting of a gasoline base stock as modified by one or more of the 23 components. By measuring the octane number and near infrared spectrum of each member of the calibration set, the octane number of any sample at the site specific for the base stock may be determined from the near infrared spectrum of the sample.

6 Claims, No Drawings

CALIBRATION OF NIR SPECTRA IN MEASURING PROPERTIES OF PETROLEUM PRODUCTS

BACKGROUND OF THE INVENTION

In recent years near infrared (NIR) spectroscopy has been used as a means of indirectly determining several characteristics of petroleum products, and especially of fuels, including properties such as octane number, Reid vapor pressure, distillation points, and so forth. Using octane number as an example, its determination via NIR involves 1) measuring the NIR spectra of a set of closely related fuels (a "calibration set") whose octane numbers have been independently determined using knock engines according to, e.g. ASTM methods 2699, 2700, and 2885, 2)developing a correlation between the NIR spectrum (i.e., absorption intensity as a function of wavelength over some wavelength range) of each member of the set and its corresponding octane number by some mathematical technique applied to the entire set (for example, multivariate analysis using principal component regression, partial least squares regression, factor analysis, multilinear regression, and so forth), and 3) applying the set of resulting correlation equations to an unknown sample of interest not in the calibration set to calculate the octane number of the sample from its measured NIR spectrum. It is clear from the foregoing that this method is a secondary method for determination of octane, as it depends on a primary standard of measurement as described in ASTM method 2699 and 2700.

The accuracy and scope of applicability of every secondary method of measurement is limited by the assumptions—whether explicit or implicit—incorporated into the relationship between the secondary and primary measurements. An important and vexing limitation on the nexus between the octane number of an unknown sample as calculated from its NIR spectrum, and the octane numbers as measured for the primary standards used for the calibration, is that the calibration set must bracket the region within which the sample lies. That is, if the members of the calibration set be viewed as independent vectors, then the sample must be at least closely approximated by a linear combination of these independent vectors. Another operational limitation which frequently applies is that the calibration set is not transferable from one refinery to another, that is, each refinery in using NIR to measure octane must develop its own calibration set. This is tantamount to saying that the octane number of any sample A will be poorly approximated by a linear combination of independent vectors (the calibration set) unless the independent vectors are obtained from the same set of samples from which A is obtained. The practical effects of these limitations are that a calibration set is best defined for each locale or refinery determining octane number by NIR, and that additional members must be added to the calibration set whenever the sample lies outside the "space" bounded by the calibration set.

DESCRIPTION OF THE INVENTION

We have made some observations recently which relax the foregoing restrictions and which facilitate the development of calibration sets. What we have noted is that the change in octane number (relative to some base value) is dominated by several individual species which can be identified from their characteristic peaks in the gas-liquid chromatogram (glc) of the fuel. Since the concentration of each species is proportional to its intensity in the glc, this observation can be expressed as $$\Delta O_c = \sum_{i=1}^{n} f_i I_i$$

where $\Delta O_c$ is the change in octane number of the sample as measured by the knock engine, $I_i$ is the relative intensity of the ith component on a glc, $f_i$ is a measure of the change in octane number associated with the ith component, and n is the number of independently varying, individual species contributing to the difference in octane and is on the order of 20. Since $$\Delta O_c = O_c - O_B$$

where $O_c$ is the octane number of the sample and $O_B$ is a base (or background) octane number, the foregoing equation can be rewritten as $$O_c = O_B + \sum_{i=1}^{n} f_i I_i \tag{1}$$

Thus, starting from an arbitrary fuel serving as a base fuel with a background octane number $O_B$ at any particular site one can develop a calibration set by the addition only of components of the glc peaks i to that base fuel. (One additionally notes that if the background fuel (with octane $O_B$) would be fuel-source/type independent—i.e., if the background contribution of octane is substantially independent of the refiner or the source of the base fuel—one could develop a calibration set using only the addition of components of the glc peaks i which would be refiner-independent and therefore transportable from one location to another.) If a number, i, of components of the glc also change covariantly, which is to say that within some group of components the concentration, C, of a member is proportional to the concentration of another member, $$C_{k+1} = rC_k \tag{2}$$

so that $$f_k C_k + f_{k+1} C_{k+1} = f_k C_k + r f_{k+1} C_k = f_k' C_k \tag{3}$$

then the octane number will be very accurately determined using a calibration set generated using only a relatively small number of components, m, where m<n (of equation 1). Note that some of these m components then would consist of two or more of the glc species in a fixed ratio; for each covariant relation (as defined above in equation 2) the number of necessary species is reduced by one (since the covarying components can be used as a single constituent). We note also that the identity of these peaks is known; vide infra. Although for the purpose of this invention the peaks are single components, they can also represent a covariant mixture of components as described above. We also note that the number n of glc peaks which contribute to variations in octane number may vary depending upon the glc conditions, e.g., the column used, temperature, flow rate, and so forth, but once the glc conditions are defined the underlying principle remains. Therefore, our invention is based on observing varying gasoline components by glc and the particular mathematical relationship and the number of species or groups of species used to develop the mathematical relationship may vary. We mention in passing that although our observations were based on glc as an analytical method, other methods, e.g., mass spectral analysis, also would suffice.

It is generally recognized that gasoline is a very complex mixture of components, with gas chromatographic (GC)

data suggesting the presence of many more than 100 individual molecular species. In developing generalized calibrations to predict the research octane number (RON) of reformates and commercial gasolines, the statistical method of partial least squares analysis was used to develop correlations between the measured near infrared (NIR) spectra and the lab-measured properties of gasoline samples in a calibration set. Since NIR responds to hydrogen atoms bonded to heavier atoms, and since only about 5 different types of hydrogen-carbon bonds were responsible for the NIR spectra observed, there was some hope that it might be possible to predict RON using only 5 factors. However, using this approach on a broad range of gasolines resulted in high correlation errors, implying that the use of only 5 factors did not provide enough information to develop a calibration which would be sufficiently general to predict the wide range of commercial gasolines likely to be encountered.

Our approach to this problem was to take a fundamental solution-chemical thermodynamic approach in order to quantify the complexity of the problem. The starting point is the recognition that RON (and motor octane number, (MON), Reid vapor pressure, (RVP), and many of the other properties we wish to correlate) was a state function of the system; no matter how the components were mixed or added, a given final composition would give the same RON. Thus a system composed of N components would have (N−1) degrees of freedom.

Given that RON, MON, etc., are intensive state functions, for gasoline consisting of N species, since $$\sum_{j=1}^{N} x_j = 1$$

where $x_j$ is the weight percent of the jth species, then $$RON = \sum_{j=1}^{N} \int_{o}^{x_j} \frac{\delta(RON)}{\delta x_j} dx_j$$

The foregoing is a general relationship, but it can be simplified if $$\frac{\delta(RON)}{\delta x_j} = \text{constant over a finite concentration range,}$$

in which case $$RON \cong (RON)_o + \sum_{j=1}^{N} \frac{\delta(RON)}{\delta x_j} \Delta x_j$$

Our data support the validity of the latter equation at least for up to 20–30% changes in concentration, $x_j$. Thus, RON changes are linear with concentration of components, and the effects of multiple components are linearly additive.

The consequence of the foregoing analysis is that a system having (N−1) degrees of compositional freedom will require (N−1) terms to describe the possible values of its RON (or other properties which are state functions). An implication of the foregoing analysis is that a truly general calibration for RON—or any other property—might be intractable if there were more degrees of freedom than could be seen in the NIR spectrum.

We next undertook to obtain the GC data for a number of gasolines to determine their level of complexity. A surprising result was the finding that samples from a given vendor showed significant composition differences for only a comparatively few species, according to GC data, no matter when they were acquired or what their octane. That is, in all samples most species were present at very low concentrations (<0.2%) or their concentrations were virtually invariant, and only a comparatively few species, 17–25 in number, showed higher values. That is, the 17–25 species present at higher (and varying) concentrations were the same for all the measured samples, although the exact amounts of each species varied from sample to sample. There also were some species present at the 1–2% level which did not vary significantly from sample to sample. The same observations were made on gasolines from other vendors. More surprisingly, when the chromatograms from three vendors were overlaid all were found to be similar. When samples from a still larger number of vendors were overlaid, the chromatograms still showed the same distribution of species.

The conclusion from these observations is that the task of developing a general calibration was much more tractable than previously expected. Subsequent experiments involving the addition of single components to a gasoline sample showed that the RON and the spectral response both were linear up to about 20–30% of the component added to the gasoline. This is a necessary condition if a linear calibration procedure is to be successful. These two sets of results together mean that it is possible (in principle) to develop a calibration set for gasolines by the addition of a relatively few components to a base gasoline. Although the vast majority of species present in gasoline are present at very low levels, in the aggregate they make up 40–60% of the gasoline and require a base-level starting gasoline for the calibration sample. The 20 or so components known to vary the most then can be added to this base-level sample, singly or in combinations, to develop calibration samples representative of the range of gasolines to be predicted using NIR.

The species found to vary significantly and which therefore control the value of the octane of gasoline around the base-level composition value are benzene, toluene, ethylbenzene, o-xylene, m-xylene, p-xylene, 1-methyl-4-ethylbenzene, 1-methyl-3-ethylbenzene, 1,2,4-trimethylbenzene, n-butane, isopentane, n-pentane, 2,2-dimethylbutane, 2-methylpentane, 3-methylpentane, n-hexane, 2-methylhexane, 2,3-dimethylpentane, 3-methylhexane, 2,2,4-trimethylpentane, methylcyclopentane, methylcyclohexane, and 1t-2c-3-trimethylcyclopentane.

From the observation that the changes in octane of gasolines—regardless of the gasoline source or origin!—may be ascribed to the relative handful of species enumerated above, one can use the foregoing set of species—or some more limited subset thereof—to develop some well-defined correlations between changes in octane number and NIR spectra. For example, let us assume that each of the foregoing species, when added in an amount up to 25 weight percent as a pure component to a base gasoline, effects a linear change in octane number, and that the change ascribed to each species is linearly independent of the octane change resulting from a change in concentration of every other species. This is equivalent to saying that octane changes are vectorially additive. One can then choose a base gasoline—the choice is arbitrary and non-critical—and add each of the pure components to this base gasoline one at a time. The pure components are added in an amount not to exceed 25 weight percent of the resulting mixture. (If several components act covariantly a mixture of the components may be used instead. For example, if the ratio of the concentrations of benzene, toluene, and the xylenes is invariant, then this group acts covariantly and may be treated as a mixture rather than as individual components for purposes of octane calibration.) After each addition of a single component one can determine 1) the change in octane number and 2) the NIR spectrum of the sample. From the resulting set of octane number change and NIR spectra as a function of component concentration change one can then use an appropriate statistical tool of one's choosing to develop the correlations between octane number and NIR spectra. Subject to the assumptions stated above, one can expect these correlations to be very accurate, tailorable to the gasolines at any given site and transportable (subject to instrumental variations) to every site using a similar base gasoline. In fact, if there could be industry-wide agreement as to a base gasoline, then the resulting calibration set would be completely transferable on an industry-wide basis with concomitant elimination of octane engines. The algorithm relating octane number and NIR spectrum obtained from this calibration set then could be used to calculate the unknown octane number of a sample.

The foregoing procedure was only exemplary of the procedures which could be used to employ the inherent advantages of the calibration set of this invention. Many other procedures may be used; the choice of procedure is not important to the success of our invention, which is the recognition that for commercial blended gasolines there are only about 25 components which account for virtually all change in octane number, and that a suitable calibration set (for some selected base gasoline) can be obtained from no more than about 25 measurements. In fact, we have found that only the 23 components named above form a suitably complete set requiring no more than 23 measurements, and that in many cases only 20 measurements suffice.

It also needs to be recognized that the foregoing description is for one very important variant of our invention, but that it is only a specific variant of a more general approach. In particular, fuels may contain other octane-enhancing additives, such as methyl tert-amyl ether (TAME), methyl tert-butyl ether (MTBE), diisopropyl ether (DIPE), ethanol, and so forth. It is clear that significant concentration variations of the foregoing in a fuel may substantially affect its octane number. Accordingly, the aforedescribed method may be suitably modified to include the octane-enhancing additive among the limited set of components added to the base gasoline feedstock whose NIR and octane number is subsequently measured and used in the development of a correlation between the measured octane number and NIR spectrum of fuels containing the octane-enhancing additive.

The method can be extended still more generally to any blended fuel where it has been determined that the change in concentration of only a limited number—say x, where x<30—of components relative to a base fuel accounts for virtually all of the change in octane number (or another property of interest such as Reid vapor pressure, distillation point, etc.) of the resulting blend. It is unnecessary that the component per se contribute to the octane number of the fuel; it is sufficient that the component leads to a change in the octane number (as by a dilution effect) of the fuel and that the component's concentration varies significantly (in the sense of an octane number or NIR spectral change resulting from the change in concentration of the component in question) from sample to sample. That is, octane changes associated with a variable concentration of a component which itself has no substantial contribution to octane number also may be correlated with NIR changes and the component's concentration by the same general method described above.

What is claimed is:

1. A method of calibrating the change in octane number of a blended gasoline from its near infrared spectrum comprising:

a) determining the octane number of a selected base blended gasoline feedstock using a knock engine;
   b) adding to the base blended gasoline feedstock an amount not to exceed 25 weight percent of at least one octane-contributing component to afford a modified base blended gasoline feedstock;
   c) measuring i) the octane number change using a knock engine and ii) the near infrared spectrum in the region of about 1100 nm to about 1600 nm of said modified base blended gasoline feedstock;
   d) repeating steps b) and c) to afford no more than about 25 measurements;
   e) determining by a suitable mathematical technique, the relation between the measured octane number changes and the near infrared spectra.

2. The method of claim 1 where said octane-contributing component is selected from the group consisting of benzene, toluene, ethylbenzene, o-xylene, m-xylene, p-xylene, 1-methyl-4-ethylbenzene, 1-methyl-3-ethylbenzene, 1,2,4-trimethylbenzene, n-butane, isopentane, n-pentane, 2,2-dimethylbutane, 2-methylpentane, 3-methylpentane, n-hexane, 2-methylhexane, 2,3-dimethylpentane, 3-methylhexane, 2,2,4-trimethylpentane, methylcyclopentane, methylcyclohexane, and 1t-2c-3-trimethylcyclopentane.

3. The method of claim 1 where no more than 23 measurements are made.

4. A method of calibrating the change in octane number of a blended gasoline from its near infrared spectrum comprising:

a) determining the octane number of a selected base blended gasoline feedstock using a knock engine;
   b) adding to the base blended gasoline feedstock an amount not to exceed 25 weight percent of at least one octane-influencing component to afford a modified base blended gasoline feedstock;
   c) measuring i) the octane number change using a knock engine and ii) the near infrared spectrum in the region of about 1100 nm to about 1600 nm of said modified base blended gasoline feedstock;
   d) repeating steps b) and c) to afford no more than about 25 measurements;
   e) determining by a suitable mathematical technique, the relation between the measured octane number changes and the near infrared spectra.

5. The method of claim 1 where said octane-influencing component is selected from the group consisting of benzene, toluene, ethylbenzene, o-xylene, m-xylene, p-xylene, 1-methyl-4-ethylbenzene, 1-methyl-3-ethylbenzene, 1,2,4-trimethylbenzene, n-butane, isopentane, n-pentane, 2,2-dimethylbutane, 2-methylpentane, 3-methylpentane, n-hexane, 2-methylhexane, 2,3-dimethylpentane, 3-methylhexane, 2,2,4-trimethylpentane, methylcyclopentane, methylcyclohexane, 1t-2c-3-trimethylcyclopentane, ethanol, diisopropyl ether, methyl tert-butyl ether, and methyl tert-amyl ether.

6. A method of calibrating the change in the value of a property of a ended fuel, relative to the value of said property in a selected base blended fuel, from the near infrared spectrum of said blended fuel comprising:

a) determining the value of said property of said selected base blended fuel by a primary method used to measure said value;
   b) adding to the selected base blended fuel an amount not to exceed 25 weight percent of at least one component which contributes to the value of said property to afford a modified base blended fuel;
   c) measuring the change in the value of said property in the modified base blended fuel by the primary measurement method and obtaining the near infrared spectrum of the modified base blended fuel in the region of about 1100 nm to about 1600 nm;
   d) repeating no more than about 30 times steps b) and c); and
   e) determining by a suitable mathematical technique the relation between changes in said property as measured by said primary method and the near infrared spectra.

* * * * *